(12) United States Patent
Perkins et al.

(10) Patent No.: US 9,943,439 B2
(45) Date of Patent: Apr. 17, 2018

(54) IRRIGATION SLEEVE AND PHACOEMULSIFICATION NEEDLE WITH SLEEVE RETENTION FEATURES

(71) Applicant: Bausch & Lomb Incorporated, Rochester, NY (US)

(72) Inventors: James T. Perkins, St. Charles, MO (US); Anthony K. Lewis, St. Charles, MO (US)

(73) Assignee: Bausch & Lomb Incorporated, Rochester, NY (US)

( * ) Notice: Subject to any disclaimer, the term of this patent is extended or adjusted under 35 U.S.C. 154(b) by 1115 days.

(21) Appl. No.: 13/661,493

(22) Filed: Oct. 26, 2012

(65) Prior Publication Data

US 2014/0121608 A1     May 1, 2014

(51) Int. Cl.
*A61F 9/007*     (2006.01)
*A61M 1/00*     (2006.01)

(52) U.S. Cl.
CPC ....... *A61F 9/00736* (2013.01); *A61M 1/0084* (2013.01); *A61B 2218/002* (2013.01); *A61F 9/00745* (2013.01); *A61M 1/008* (2013.01)

(58) Field of Classification Search
CPC .. A61F 9/00736; A61M 1/0084; A61M 1/008
USPC ..... 604/22, 164.08, 171, 172, 192, 198, 521
See application file for complete search history.

(56) References Cited

U.S. PATENT DOCUMENTS

| | | | |
|---|---|---|---|
| 5,286,256 A | 2/1994 | MacKool | |
| 5,505,693 A * | 4/1996 | Mackool | ......................... 604/22 |
| 5,807,310 A | 9/1998 | Hood | |
| 5,935,096 A | 8/1999 | Barrett | |
| 6,592,541 B1 | 7/2003 | Kurwa | |
| 7,014,629 B2 | 3/2006 | MacKool | |
| 7,329,261 B2 | 2/2008 | Perkins | ......................... 606/107 |
| 8,435,248 B2 | 5/2013 | Herman | ......................... 606/107 |
| 2006/0047241 A1 | 3/2006 | Boukhny | |
| 2007/0073213 A1* | 3/2007 | Brown | ......................... 604/22 |
| 2010/0121260 A1 | 5/2010 | Ghannoum et al. | |
| 2010/0174162 A1 | 7/2010 | Gough et al. | |
| 2012/0157936 A1 | 7/2012 | Kern | |
| 2012/0172786 A1 | 7/2012 | MacKool | |

(Continued)

FOREIGN PATENT DOCUMENTS

JP     2012-508612     4/2012

OTHER PUBLICATIONS

European Search Report for 13848612 dated May 24, 2016 pp. 7.

(Continued)

*Primary Examiner* — Bhisma Mehta
*Assistant Examiner* — Benjamin Koo
(74) *Attorney, Agent, or Firm* — Michael L. Smith

(57) ABSTRACT

A combination of an irrigation sleeve 20 and a phacoemulsification needle 22. The irrigation sleeve 20 has a proximal end 32 and a distal end 30, the proximal end for attachment to a surgical handpiece. The phacoemulsification needle 22 has a proximal end 26, a distal end 24, and a lumen 38 spanning a length of the needle 22 from the proximal end 26 to the distal end 24. The needle proximal end 26 is for connection to the surgical handpiece, and the needle 22 has structure 44 proximate the needle distal end 24 for retaining the sleeve distal end 30 near the needle distal end 24.

1 Claim, 3 Drawing Sheets

(56) References Cited

U.S. PATENT DOCUMENTS

2012/0191034 A1\* 7/2012 Akahoshi ........................ 604/22

OTHER PUBLICATIONS

International Search Report and Written Opinion for PCT/US2013/066806 dated Jan. 17, 2014 pp. 15.
International Preliminary Report on Patentability for PCT/US2013/066806 dated Apr. 28, 2015 pp. 6.

\* cited by examiner

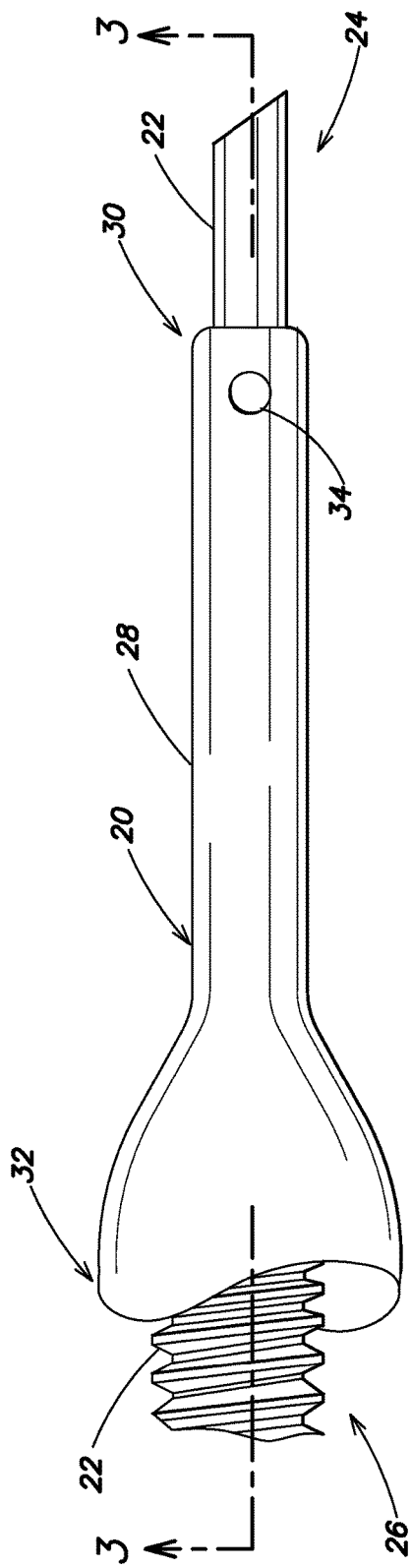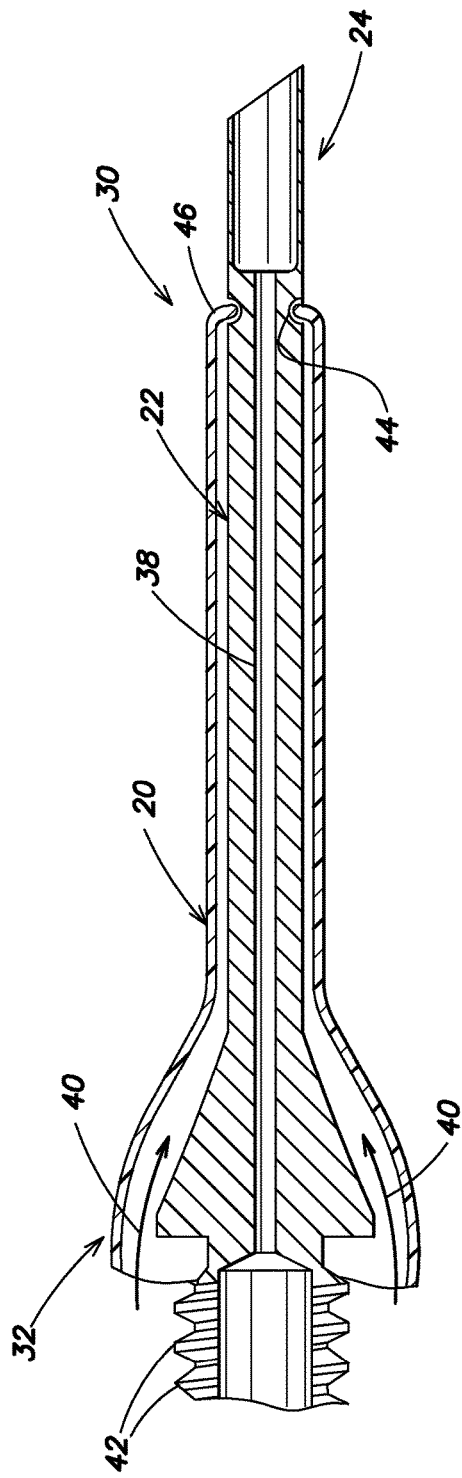

IRRIGATION SLEEVE AND PHACOEMULSIFICATION NEEDLE WITH SLEEVE RETENTION FEATURES

BACKGROUND

1. Field

The present embodiment relates to phacoemulsification sleeves and needles and, more particularly, to combinations of sleeves and needles with features for retaining the attachment of the sleeve to the needle in a desired position during and after insertion through an incision.

2. Description of the Related Art

It is well known in the art to use a bi-axial phacoemulsification (phaco) handpiece. A phaco handpiece has a phaco needle attached to a distal end of the handpiece with a flexible irrigation sleeve surrounding most of the phaco needle and also attached to the handpiece. The sleeve typically carries irrigation fluid from an outlet in the handpiece to a surgical site. The irrigation fluid flows between the inside of the sleeve and the outside of the needle, and into a surgical site through ports formed in the sleeve. The irrigation fluid helps cool the needle during use, and also replaces fluid aspirated from the surgical site through a lumen in the needle to prevent the eye globe from collapsing during surgery. Thus the needle and sleeve provide two functions, irrigation and aspiration, in a bi-axial manner.

The irrigation sleeve is typically formed of compliant material, such as silicone or other relatively soft, compressible materials, so that the sleeve will not damage the tissue at the incision interface and also for the purpose of forming at least a partial seal at the incision to minimize fluid leaking from the eye during surgery.

Current trends in ophthalmic surgery are demanding ever smaller diameter needles and smaller incisions. It is believed that smaller incisions lead to less change in corneal curvature and better visual acuity post-operation. These smaller incisions have led to tighter interfaces with the sleeves and needles. A problem, becoming more prevalent, is that the sleeve accordions at the incision, as the surgeon attempts to insert the sleeve and needle through the incision. This problem is shown at FIG. 1. A needle 10 has passed through an incision 12 in an eye 14, but a sleeve 16 has accordioned at 18 outside the eye 14. Needle 10 is attached to a phaco handpiece 20 in a known manner, typically via a threaded connection, as shown. It is critical that sleeve 16 pass through incision 12 and into the eye 14 along with needle 10, so that sleeve 16 can protect the eye tissue from damage and to provide irrigation fluid into the eye 14.

Therefore, it would be desirable to provide a combination of an irrigation sleeve and a needle that would assist in retaining the sleeve in a desired position, as the sleeve and needle are inserted through an incision.

BRIEF DESCRIPTION OF THE DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

FIG. 2 is an elevation of an irrigation sleeve and phaco needle combination, in accordance with the present disclosure;

FIG. 3 is a sectional view of FIG. 2 taken along lines 3-3;

DETAILED DESCRIPTION

Figure 1:
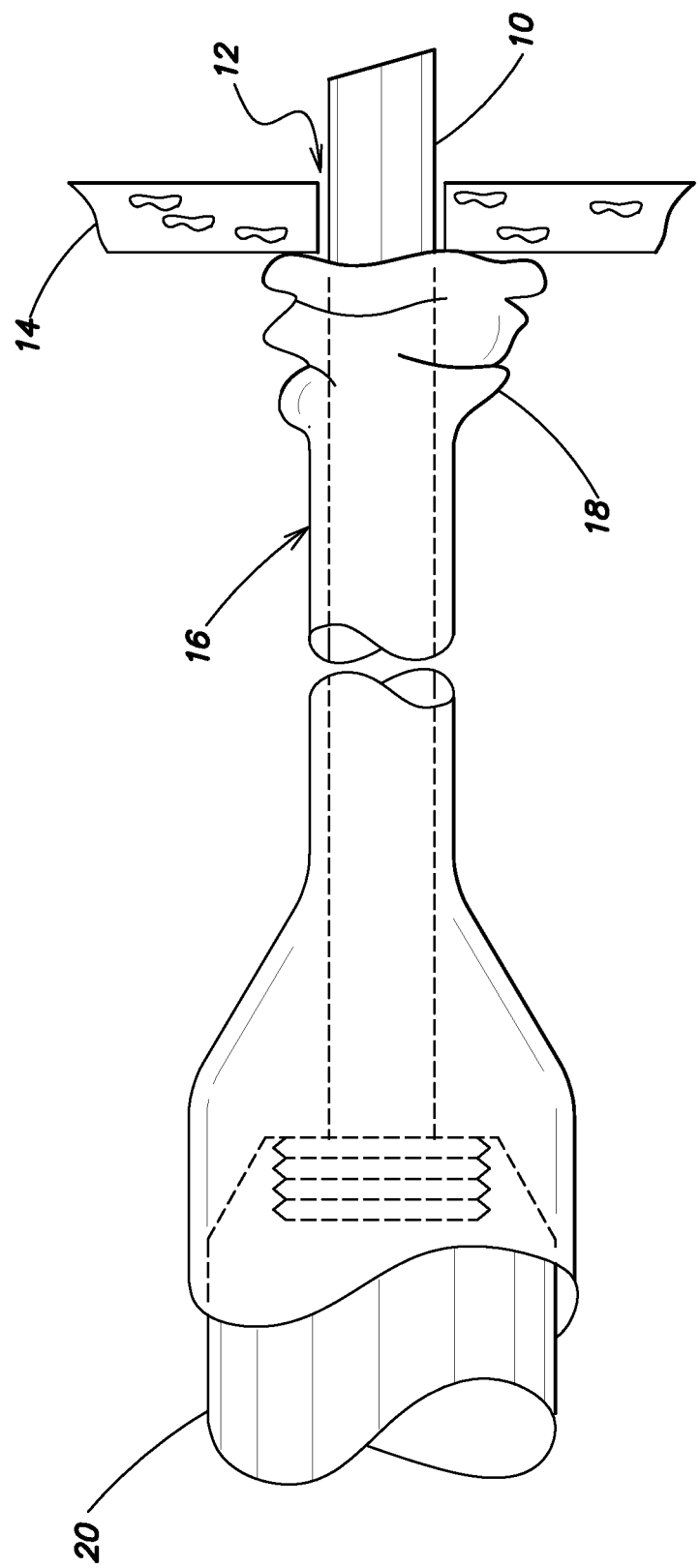
FIG. 1 is an elevation of a prior art irrigation sleeve and phaco needle.

FIG. 2 shows a phacoemulsification needle sleeve 20, in accordance with the present disclosure. Sleeve 20 is attached to a phacoemulsification needle 22 having a distal end 24 and a proximal end 26. Proximal end 26 is typically attached to a conventional phacoemulsification handpiece (not shown), which may or may not include a port for delivering irrigation fluid between the phacoemulsification needle sleeve 20 and needle 22. Sleeve 20 includes an elongated, resilient essentially tubular body portion 28 having a distal end 30 and a proximal end 32 for surrounding a portion of a shaft of a phacoemulsification needle 22. Sleeve proximal end 32 includes an enlarged section, as shown, formed on the proximal end of the body portion 28 for surrounding a hub (shown below in FIG. 3) of the needle 22, and for attachment to a surgical handpiece (not shown). The sleeve distal end 30 is retained by needle structure (shown below in FIG. 3) proximate needle distal end 24 for retaining the sleeve distal end 30 near the needle distal end 24. The sleeve 20 also typically includes at least one irrigation port 34 (see FIG. 2) formed proximate the sleeve distal end 30.

The sleeve 20 is typically formed of silicone or other pliable, compressible, resilient materials suitable for use in surgery. In this way, sleeve 20 performs both an insulative and sealing function for use during cataract surgery. FIG. 3 shows a cut-away view of FIG. 2 taken along line 3-3. As can be seen, enlarged section of the proximal end 32 surrounds a phaco needle hub 36 of needle 22. During surgery, emulsified cataract tissue and irrigation fluid are aspirated through lumen 38 spanning a length of the needle 22 from the proximal end 26 to the distal end 24 into a phaco handpiece, not shown, and eventually into a collection reservoir of a pumping system of an ophthalmic surgical system (also not shown), such as that available from Bausch & Lomb Incorporated. Irrigation fluid may be introduced to surround needle 22 and be contained by sleeve 20 and will initially flow in the direction of arrows 40. The introduction of such irrigation fluid provides for more insulative and sealing effects for sleeve 20 than without such fluid being introduced between needle 22 and the sleeve 20. The needle proximal end 26 typically includes a threaded hub 42 for mating connection to a threaded section of the surgical handpiece (not shown). The sleeve distal end 30 is retained by needle structure 44 near the needle distal end 24.

Needle structure 44 of FIG. 3, is in the form of an annular groove, as shown, for mating engagement with a flange 46 of the sleeve 20. Groove 44 and flange 46 cooperate to prevent the sleeve accordion shown in FIG. 1. By retaining sleeve distal end 30 near needle distal end 24 as the sleeve 20 and needle 22 are inserted through an incision, the sleeve will be properly positioned to provide irrigation fluid to the eye during surgery, as well as provide its insulative and sealing properties. This increases the efficiency of the surgery and minimizes the likelihood that a surgeon will need to halt surgery and manipulate the sleeve, needle, and incision to insert the sleeve through the incision. This results in less trauma to the tissue at the incision. Retaining the sleeve in the groove 44 also provides a consistent position of the sleeve distal end 30 relative to the needle distal end 24 which assists the surgeon in visualization of the surgical site. Groove 44 may have a cross-sectional shape other than the rounded shape shown, such as square, triangular, or other geometric shapes.

Figure 4:
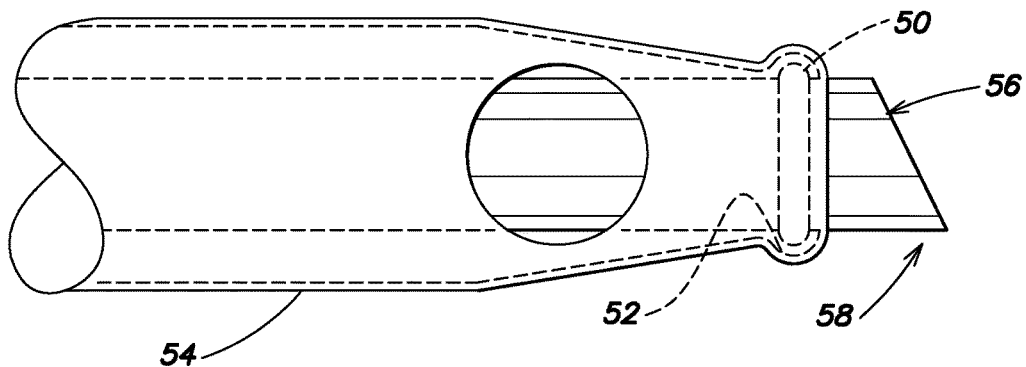
FIG. 4 is a partial elevation of an alternative embodiment of an irrigation sleeve and phaco needle combination, in accordance with the present disclosure.
Figure 5:
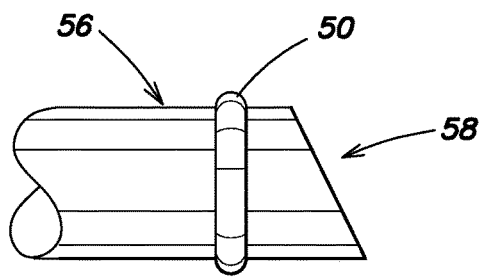
FIG. 5 is a partial elevation of the phaco needle of FIG. 4.

FIGS. 4 and 5 disclose an alternate embodiment where the retaining structure is an annular boss 50 for mating engagement with a groove 52 of a sleeve 54. Boss 50 may be formed on needle 56 by any known method, such as molding, machining, or other methods. Boss 50 may also be a separate ring that is adhered to or frictionally attached to needle 56. Boss 50 may also have cross-sectional shapes other than the rounded shape shown, such as square, triangular, or other geometric shapes. The groove 52 should have a shape sufficiently mating to the boss 50, so that sleeve 54 will be retained near the needle distal end 58.

Figure 6:
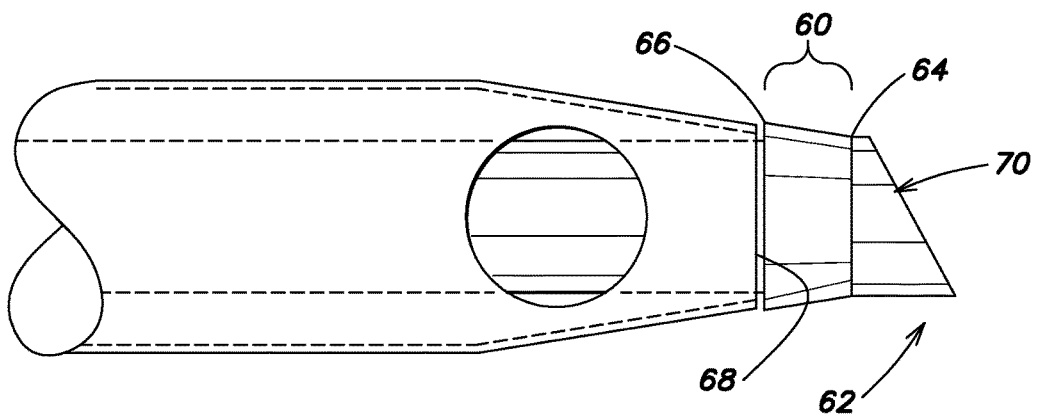
FIG. 6 is a partial elevation of another embodiment of an irrigation sleeve and phaco needle combination, in accordance with the present disclosure.

FIG. 6 illustrates another embodiment where the retaining structure is a tapered section 60 proximate the needle distal end 62, such that an outer diameter of the tapered section increases from a distal point 64 to a proximal point 66, such that the outer diameter of the tapered section 60 at the proximal point 66 is greater than an outer diameter of the sleeve distal end 68. Tapered section 60 can be formed on needle 70 by any know method, including those identified above with respect to forming boss 50. It is important that the outer diameter at proximal point 66 is greater than the outer diameter of the sleeve distal end 68, so that the sleeve distal end 68 will not catch on the incision and accordion as the needle and sleeve combination is inserted through the incision. The tapered section 60 also provides for a ramp or wedge to spread the incision with minimal tissue trauma and allow the sleeve to pass through the incision without catching on the incision.

The embodiments shown above allow an irrigation sleeve and phaco needle combination to be easily inserted through an incision of less than 2 mm in length. The needles and sleeves of all the embodiments are essentially the same, except for the differences in the retaining structure and the sleeve distal ends.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

We claim:

1. A combination of an irrigation sleeve and a phacoemulsification needle comprising:
   an irrigation sleeve having a proximal end and a distal end, the proximal end for attachment to a surgical handpiece;
   a phacoemulsification needle having a proximal end, a distal end and a lumen spanning a length of the needle from the proximal end to the distal end;
   wherein the needle proximal end is for connection to the surgical handpiece and the needle has structure forming a tapered section proximate the needle distal end such that an outer diameter of the tapered section increases from a distal point to a proximal point; and
   wherein the irrigation sleeve distal end surrounds the needle adjacent the tapered section proximal point such that the outer diameter of the tapered section at the proximal point is greater than an outer diameter of the sleeve distal end.

\* \* \* \* \*